US00PP35978P2

(12) United States Plant Patent
Blaker

(10) Patent No.: US PP35,978 P2
(45) Date of Patent: Jul. 9, 2024

(54) STRAWBERRY PLANT NAMED 'SB 15.001.011'

(50) Latin Name: *Fragaria ananassa*
Varietal Denomination: SB 15.001.011

(71) Applicant: Strawberry Sciences, LLC, Watsonville, CA (US)

(72) Inventor: Kendra M. Blaker, Archer, FL (US)

(73) Assignee: Strawberry Sciences, LLC, Watsonville, CA (US)

( * ) Notice: Subject to any disclaimer, the term of this patent is extended or adjusted under 35 U.S.C. 154(b) by 0 days.

(21) Appl. No.: 18/220,784

(22) Filed: Jul. 11, 2023

(51) Int. Cl.
*A01H 5/08* (2018.01)
*A01H 6/74* (2018.01)

(52) U.S. Cl.
USPC ..... Plt./208

(58) Field of Classification Search
USPC ..... Plt./208

CPC ..... A01H 5/08; A01H 5/00; A01H 6/7409; A01H 6/74
See application file for complete search history.

(56) References Cited

U.S. PATENT DOCUMENTS

PP30,564 P3 * 6/2019 Whitaker ..... A01H 5/08 Plt./208

OTHER PUBLICATIONS

International Code of Nomenclature for Cultivated Plants Scripta Horticulturae No. 10, Eighth Edition 2009, 3 cover pp., iii-iv and pp. 29-30. (Year: 2009).*

* cited by examiner

*Primary Examiner* — June Hwu
(74) *Attorney, Agent, or Firm* — Foley & Lardner LLP

(57) ABSTRACT

This invention relates to a new and distinct variety of strawberry plant named 'SB 15.001.011'. This new strawberry plant named 'SB 15.001.011' is primarily adapted to the growing conditions of West Central Florida, and is primarily characterized by achenes set even with or slightly below the surface of the fruit; vigorous plant habit; very high marketable yield; early time of first flower and fruit; and large berry size.

4 Drawing Sheets

Latin name of the genus and species of the plant claimed: *Fragaria ananassa.*
Variety denomination: 'SB 15.001.011'.

BACKGROUND OF THE INVENTION

The present invention relates to a new and distinct strawberry variety named 'SB 15.001.011'. This new variety is a result of a controlled cross made in 2015 in an ongoing breeding program between the unreleased, unpatented strawberry breeding selection designated 'SB_11_037-083' as the seed (female) parent, and the unreleased, unpatented strawberry breeding selection designated 'SB_11_140-047' as the pollen (male) parent. The variety is botanically known as *Fragaria ananassa.*

The seedling resulting from the aforementioned cross was selected from a controlled breeding plot in Wimauma, (Hillsborough County), Florida in the fall/winter of 2016-2017. After its selection, the new variety was asexually propagated by stolons in both Macdoel (Siskiyou County), California and Manteca (San Joaquin County), California. The new variety was extensively tested over the next several years in fruiting fields in Wimauma, (Hillsborough County), Florida. This propagation has demonstrated that the combination of traits disclosed herein as characterizing the new variety are fixed and remain true-to-type through successive generations of asexual reproduction.

BRIEF SUMMARY OF THE INVENTION

'SB 15.001.011' is primarily adapted to the climate and growing conditions of West Central Florida. The subtropical climate of West Central Florida provides the day length and moderate temperatures needed to produce an early yielding, vigorous plant and maintain fruit quality during the fall and winter production months. Damage to fruit and young leaves has not been observed in temperatures at or below 95° F. (35° C.). No winter damage has been observed on fruiting plants in off-cycle (winter) production regions of USDA climate zones 9b and above. In climate zones below this, winter hardiness is unknown for 'SB 15.001.011'. 'SB 15.001.011' is not drought tolerant and requires frequent irrigation to maintain proper plant health.

The following traits have been repeatedly observed and are determined to be unique characteristics of 'SB 15.001.011', which in combination distinguish this strawberry plant as a new and distinct variety:

1. Achenes typically set even with or slightly below the surface of the fruit;
2. Vigorous plant habit;
3. Very high marketable yield;
4. Early time of first flower and fruit; and
5. Large berry size.

'Florida Brilliance' (U.S. Plant Pat. No. 30,564) is currently the dominant strawberry variety in Hillsborough County, Florida. The fruits of 'SB 15.001.011' are similar in skin integrity, the level of sunken seeds, and berry shape to 'Florida Brilliance', but the fruit color of 'Florida Brilliance' is slightly lighter than the fruits of 'SB 15.001.011'. The plants of 'SB 15.001.011' are similar in vigor, openness of architecture, and uniformity to 'Florida Brilliance', but have more runners per plant than 'Florida Brilliance'. In side-by-side comparisons from the 2022-2023 season (Nov. 21, 2022 to Feb. 24, 2023), 'SB 15.001.011' compares with 'Florida Brilliance' (U.S. Plant Pat. No. 30,564) in the following combination of characteristics as described in Table 1.

TABLE 1

| Characteristic | 'SB 15.001.011' | 'Florida Brilliance' (U.S. Plant Pat. No. 30,564) |
|---|---|---|
| Nov.-Dec. marketable yield (gm/plt) | 138 | 212 |
| Season marketable yield (gm/plt) | 303 | 408 |
| Nov.-Dec. average berry size (gm) | 18.7 | 17.1 |
| Average runners/plant | 4.0 | 2.9 |

For identification, a series of molecular markers have been determined for this new variety.

'SB 15.001.011' compares with its parents, 'SB_11_037-083' and 'SB_11_140-047', by the following combination of characteristics as described in Tables 2 and 3.

TABLE 2

| Characteristic | 'SB 15.001.011' | 'SB_11_037-083' |
|---|---|---|
| Fruit: size | Large | Large |
| Fruit: marketable yield | Very high | Medium |
| Plant: runners/plant | 1-5 | 10-15 |
| Plant: vigor | Strong | Very strong |

TABLE 3

| Characteristic | 'SB 15.001.011' | 'SB_11_140-047' |
|---|---|---|
| Fruit: size | Large | Medium |
| Fruit: marketable yield | Very high | Low |
| Fruit: color | Red | Light orange |
| Plant: vigor | Strong | Moderately strong |

BRIEF DESCRIPTIONS OF THE PHOTOGRAPHS

The accompanying color photographs illustrate the overall appearance of typical specimens of the new strawberry variety 'SB 15.001.011' at various stages of development, as true as it is reasonably possible with color reproductions of this type. Color in the photographs may differ slightly from the color value cited in the botanical descriptions which accurately describe the color of 'SB 15.001.011'. The depicted plant and plant parts of the new strawberry variety 'SB 15.001.011' are approximately four months old. The photographs were taken in Hillsborough County, Florida.

DETAILED BOTANICAL DESCRIPTION

Figure 1:
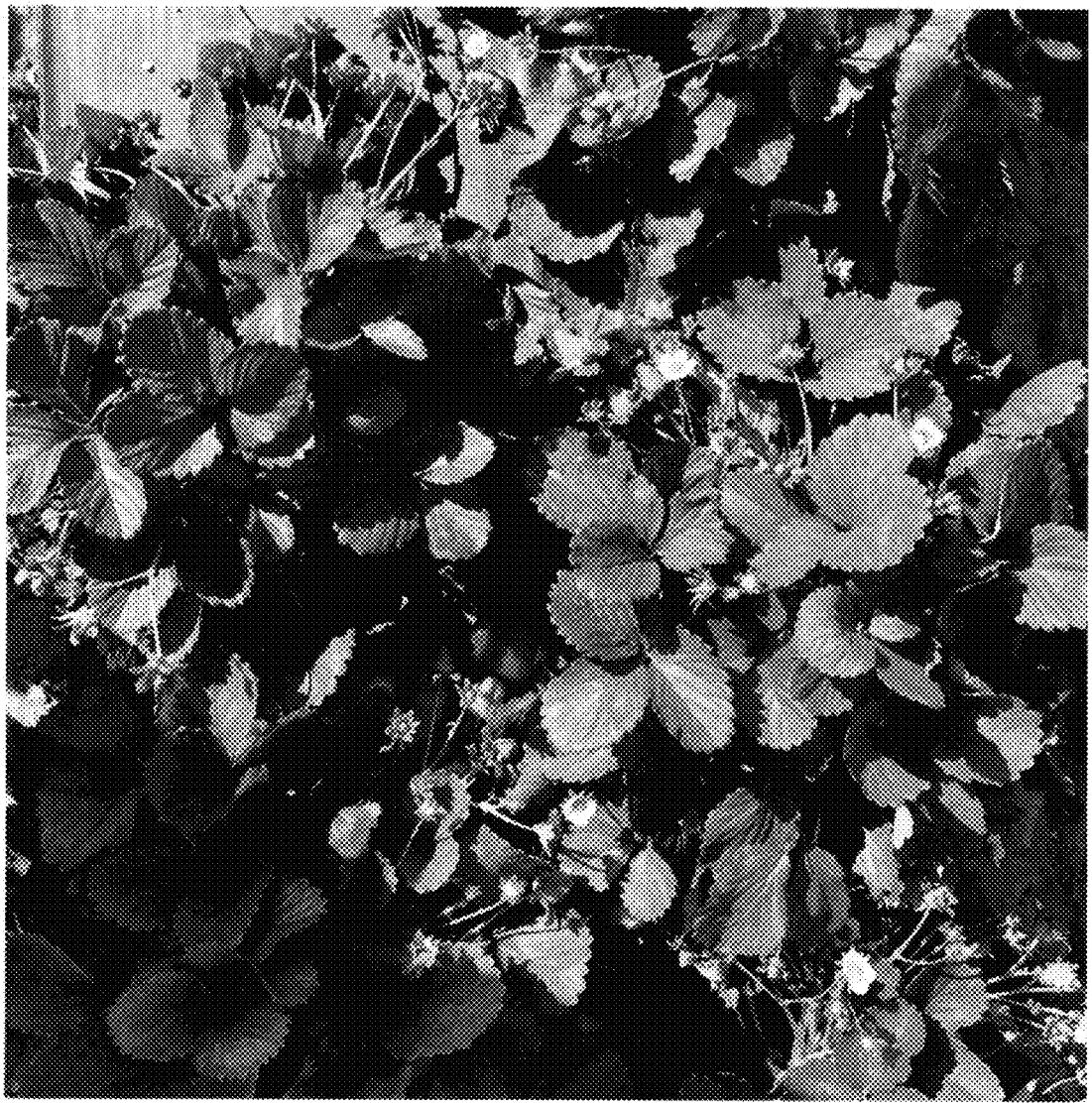
FIG. 1 shows typical fruiting field characteristics of 'SB 15.001.011', taken in the month of February 2023.
Figure 2:
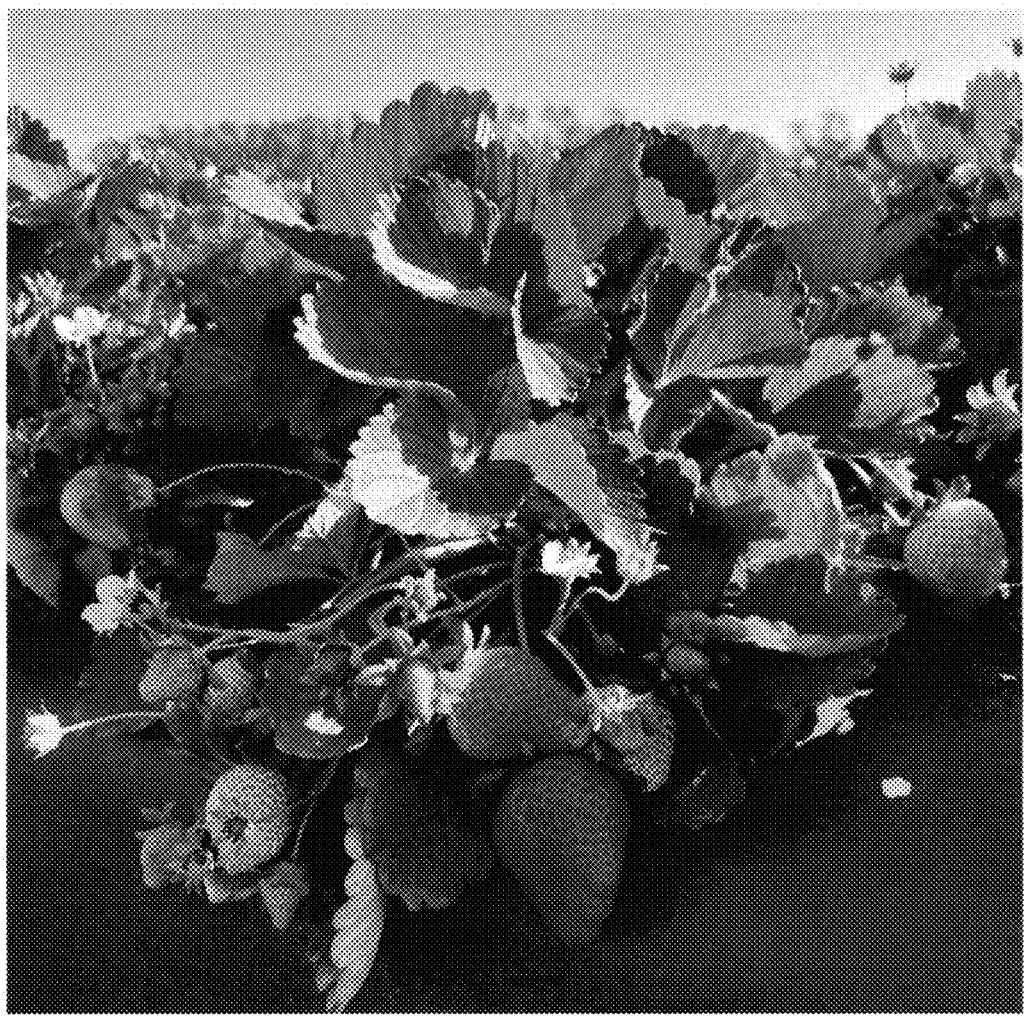
FIG. 2 shows a close-up view of a typical plant of 'SB 15.001.011', taken in the month of February 2023.
Figure 3:
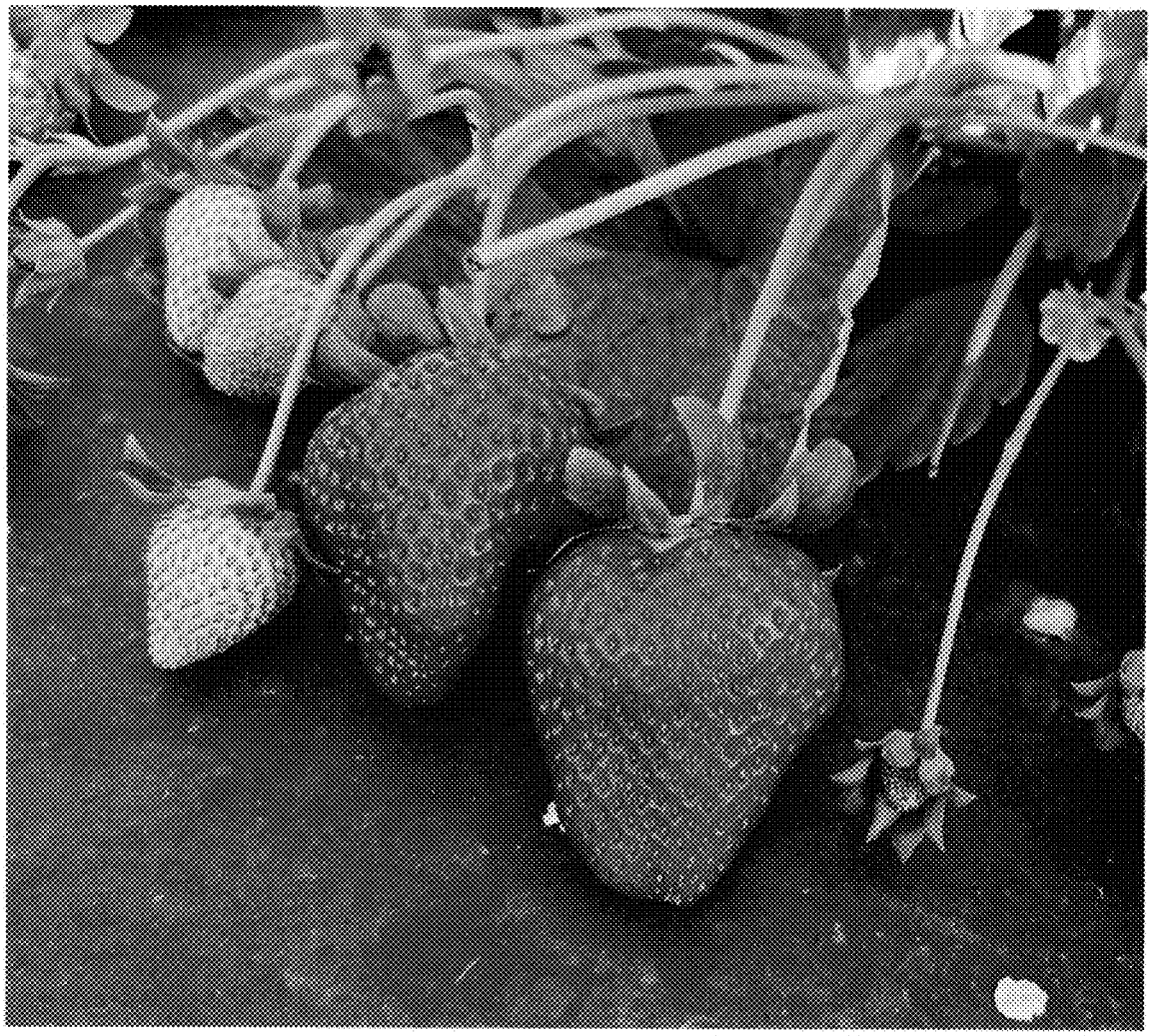
FIG. 3 shows typical mature and immature field fruit of 'SB 15.001.011', taken in the month of February 2023.
Figure 4:
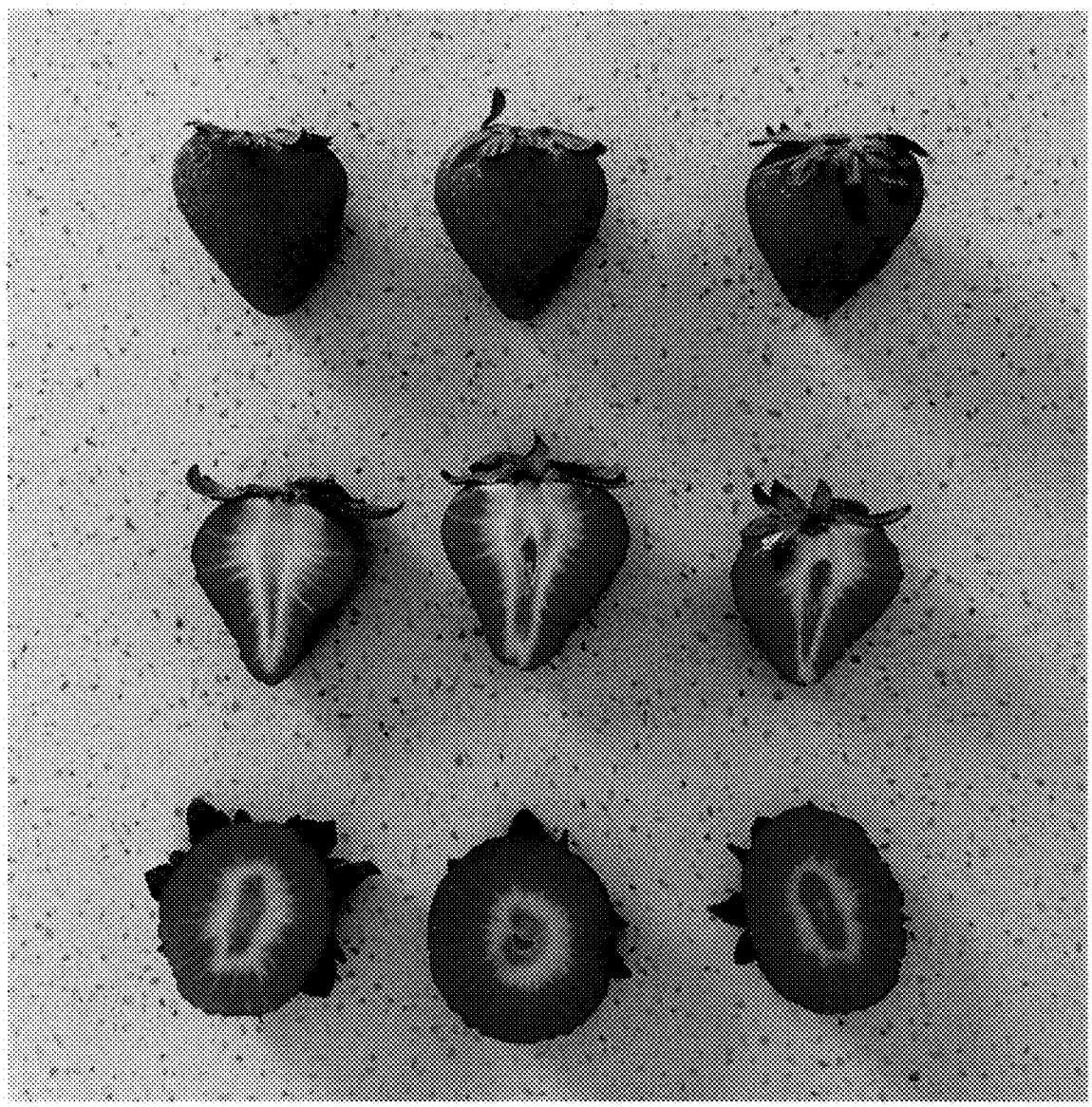
FIG. 4 shows typical internal and external mature fruit characteristics of 'SB 15.001.011', taken in the month of February 2023.

The new variety 'SB 15.001.011' has not been observed under all possible environmental conditions. The characteristics of the new variety 'SB 15.001.011' may vary in detail, depending upon variations in environmental factors, including weather (temperature, humidity and light intensity), day length, soil type and location. In addition, the characteristics of any parental variety or comparison variety included in Table 1 of the present invention may vary in detail, depending upon variations in environmental factors, including weather (temperature, humidity and light intensity), day length, soil type and location.

The aforementioned photographs, together with the following description of the new variety 'SB 15.001.011', unless otherwise noted, are based on observations taken during the 2022-2023 growing season in Hillsborough County, Florida. These measurements and ratings were taken from plants of 'SB 15.001.011' dug from a high-elevation nursery located in Siskiyou County, California during mid-September 2022 and planted approximately four to five days later in Hillsborough County, Florida. The approximate age of the observed plants is four months. Yield observations including average weight and marketable yield, along with fruit quality characteristics including soluble solids, were measured during the 2022-2023 growing season. Flower measurements and characteristics are from secondary flowers unless otherwise noted. Fruit characteristics and measurements are from secondary fruit, unless otherwise noted.

Where noted, color terminology follows The Royal Horticultural Society Colour Chart, London (2015).

The following characteristics describe fruit, plant, stolon, foliage, fruiting truss, flower, reproductive organs and pest and disease characteristics of the new strawberry 'SB 15.001.011'.

Fruit characteristics:

*Color of mature fruit*.—RHS N45A (red group).

*Color of internal flesh (excluding core)*.—RHS 44A (red group).

*Color of core*.—RHS 44C (red group).

*Average length (cm)*.—3.9.

*Average width (cm)*.—3.8.

*Size*.—Large.

*Average length/width ratio*.—1.06 (slightly longer than broad).

*Average calyx diameter (cm)*.—3.4.

*Season average weight (gm)*.—25.7.

*Achene color, shaded side*.—RHS 145A (yellow-green group).

*Achene color, sun-exposed side*.—RHS N144A (yellow-green group).

*Average achene weight (mg)*.—<0.6.

*Average achenes per berry*.—291.

*Average achene length (mm)*.—1.4.

*Average achene width (mm)*.—0.8.

*Season marketable yield (gm/plant)*.—408.

*Predominant shape*.—Conical.

*Difference in shape between primary and secondary fruit*.—Moderate.

*Band without achenes*.—Ranges from absent to very narrow.

*Evenness of surface*.—Even or very slightly uneven.

*Evenness of color*.—Even or very slightly uneven.

*Glossiness*.—Medium.

*Insertion of achenes*.—Ranges from below surface to even with surface.

*Position of calyx attachment*.—Inserted.

*Attitude of sepals*.—Ranges from outward to downward.
*Size of calyx in relation to fruit diameter*.—Slightly smaller.
*Adherence of calyx* (*when fully ripe*).—Medium.
*Firmness of flesh* (*gf*).—321.
*Distribution of red color of the flesh*.—Marginal and central.
*Hollow center expression*.—Moderate.
*Average cavity length* (*mm*).—12.9.
*Average cavity width* (*mm*).—3.9.
*Soluble solids* (*% brix*).—5.76.
*Time of first flowering*.—Early (early to mid-October in Hillsborough County, Florida).
*Flowering season*.—October-February.
*Time of first fruit*.—Early (mid-November in Hillsborough County, Florida).
*Fruiting season*.—November-March.
*Post-harvest fruit longevity*.—9-11 days, if stored according to industry standards.
*Market use*.—fresh fruit consumption.
*Type of bearing*.—Not remontant.

Plant characteristics:
*Average height* (*cm*) —22.9.
*Average spread* (*cm*).—38.
*Size*.—Ranges from medium to large.
*Habit*.—Upright.
*Density*.—Medium.
*Vigor*.—Ranges from medium to strong.

Stolon characteristics:
*Color*.—RHS N144C (yellow-green group).
*Anthocyanin coloration*.—RHS 182B (greyed-red group).
*Anthocyanin intensity*.—Ranges from medium to weak.
*Pubescence*.—Ranges from medium to sparse.
*Attitude of hairs*.—Upward.
*Average quantity in nursery* (*per square foot*).—8 (medium).
*Average diameter at the bract* (*mm*).—2.2 (medium).
*Average length* (*cm*).—9.25.

Terminal leaflet characteristics:
*Color of upper surface*.—N137A (green group).
*Color of underside*.—RHS 138A (green group).
*Average length* (*cm*).—8.6.
*Average width* (*cm*).—7.8.
*Average area terminal* ($cm^2$).—66.9.
*Average length/width ratio*.—1.1 (longer than broad).
*Shape of base*.—Obtuse.
*Margins* (*shape of teeth*).—Serrate to crenate.
*Average serrations per leaf*.—18.3.

Foliage characteristics:
*Color of upper surface*.—RHS N137A (green group).
*Color of underside*.—RHS 138A (green group).
*Number of leaflets*.—3.
*Leaf size*.—Large.
*Average length* (*cm*).—12.5.
*Average width* (*cm*).—14.9.
*Average area foliage* ($cm^2$).—184.9.
*Shape in cross section*.—Concave.
*Texture/interveinal blistering*.—Medium.
*Leaf glossiness*.—Medium.
*Leaf variegation*.—Absent.
*Venation pattern*.—Pinnate.
*Apex descriptor*.—Obtuse.

Petiole characteristics:
*Petiole color*.—RHS 144B (yellow-green group).
*Average length* (*cm*).—16.4.
*Average diameter* (*mm*).—2.5.
*Petiolule color*.—RHS 144B (yellow-green group).
*Petiolule average length* (*mm*).—15.5.
*Average petiolule diameter* (*mm*).—1.58.
*Attitude of hairs*.—Strongly outward.
*Texture*.—Moderately smooth.
*Frequency of bract leaflets*.—Ranges from 0 to 2 (50% occurrence).
*Size of bract leaflets* (*none, and/or small to large*).—Ranges from none to medium.
*Pubescence*.—Ranges from moderate to sparse.

Stipule characteristics:
*Color*.—RHS 145A (yellow-green group).
*Anthocyanin coloration*.—RHS 182A (greyed-red group).
*Anthocyanin intensity*.—Weak.
*Average length* (*mm*).—36.9.
*Average width* (*mm*).—9.4.
*Base descriptor*.—Truncate.
*Apex descriptor*.—Obtuse.
*Shape*.—Triangular.
*Margin*.—Entire.
*Texture*.—Smooth.

Fruiting truss characteristics:
*Anthocyanin coloration*.—N/A.
*Anthocyanin intensity*.—Absent.
*Pubescence* (*none to heavy*).—Medium.
*Attitude at first pick*.—Prostrate.
*Position relative to foliage*.—Ranges from level with to below.
*Flower quantity* (*average per plant season long*).—54.3 (many).
*Average fruits per truss*.—17.3.
*Pedicel attitude of hairs*.—Slightly outward.
*Average pedicel length* (*cm*).—12.75.
*Average pedicel diameter* (*mm*).—2.03.
*Pedicel texture*.—Smooth.
*Pedicel color*.—RHS 144B (yellow-green group).
*Average peduncle length* (*cm*).—6.7.
*Average peduncle diameter* (*mm*).—3.2.
*Peduncle texture*.—Moderately Smooth.
*Peduncle color*.—145B (yellow-green group).

Flower characteristics:
*Flower bud shape*.—Pyriform.
*Average flower bud length* (*mm*).—17.67.
*Average flower bud diameter* (*mm*).—6.72.
*Flower bud color*.—RHS 145A (yellow-green group).
*Flower depth* (*mm*).—5.6.
*Corolla* (*flower*) *average diameter* (*mm*).—26.4 (ranges from medium to large).
*Upper petal color*.—RHS NN155C (white group).
*Lower petal color*.—RHS NN155D (white group).
*Petal shape*.—Orbicular.
*Petal apex descriptor*.—Obtuse.
*Petal margin*.—Entire.
*Petal base*.—Decurrent.
*Petal texture*.—Smooth.
*Petal average length* (*mm*).—11.5.
*Petal average width* (*mm*).—11.7.
*Petal average length/width ratio*.—0.98 (broader than long).
*Average petals per flower*.—6.2.

*Relative position of petals* (*flowers with* 5 *or* 6 *petals*) .—Overlapping.
*Upper sepal color*.—RHS 137A (green group).
*Lower sepal color*.—RHS 137D (green group).
*Sepal shape*.—Cuneate.
*Sepal apex descriptor*.—Obtuse.
*Sepal margin*.—Serrate.
*Sepal texture*.—Smooth.
*Sepal average length* (*mm*).—18.7.
*Sepal average width* (*mm*).—8.2.
*Sepal average length/width ratio*.—2.3.
*Average sepals per flower*.—11.8.
*Calyx average diameter* (*mm*).—47.0.
*Size of calyx relative to corolla*.—Larger.
*Size of inner calyx relative to outer calyx*.—Smaller.

Reproductive organs:
*Receptacle color*.—RHS 146D (yellow-green group).
*Pollen color*.—RHS 13A (yellow group).
*Stamen*.—Present.
*Average filament length* (*mm*).—2.8.
*Filament color*.—RHS 157A (green-white group).
*Average anthers per flower*.—26.
*Average anther length* (*mm*).—1.3.
*Anther shape*.—Ovoid.
*Anther color*.—RHS 21A (yellow-orange color).
*Average pistils per flower*.—291.
*Pistil length* (*mm*).—0.5-1.5.
*Style length* (*mm*).—0.5 to 1.
*Style color*.—RHS 3C (yellow group).
*Stigma diameter* (*mm*).—<0.1.
*Stigma shape*.—Simple.
*Ovary color*.—RHS 1C (green-yellow group).
*Pollen amount*.—Abundant.

Disease reactions:
*Colletotrichum crown rot* (*colletotrichum gloeosporioides*).—Susceptible.
*Pestalotia leaf spot and fruit rot* (*neopestalotiopsis sp.*).—Susceptible.
*Phytophthora crown rot* (*phytophthora cactorum*).—Susceptible.

I claim:

1. A new and distinct strawberry plant named 'SB 15.001.011', as herein described and illustrated by the characteristics set forth above.

* * * * *